United States Patent
Baroni et al.

(10) Patent No.: US 8,153,693 B2
(45) Date of Patent: Apr. 10, 2012

(54) COMPOUNDS FOR THE SELECTIVE TREATMENT OF THE INTESTINAL IMMUNO-INFLAMMATORY COMPONENT OF THE CELIAC DISEASE

(75) Inventors: Sergio Baroni, Bergamo (IT); Salvatore Bellinvia, Pordenone (IT)

(73) Assignee: Giuliani International Limited, Dublin (IE)

( * ) Notice: Subject to any disclaimer, the term of this patent is extended or adjusted under 35 U.S.C. 154(b) by 0 days.

(21) Appl. No.: 12/810,159

(22) PCT Filed: Dec. 23, 2008

(86) PCT No.: PCT/EP2008/068265
§ 371 (c)(1),
(2), (4) Date: Aug. 16, 2010

(87) PCT Pub. No.: WO2009/080828
PCT Pub. Date: Jul. 2, 2009

(65) Prior Publication Data
US 2010/0305077 A1  Dec. 2, 2010

(30) Foreign Application Priority Data
Dec. 24, 2007  (IT) .............................. MI2007A2429

(51) Int. Cl.
*A61K 31/196* (2006.01)
*A61K 31/166* (2006.01)
(52) U.S. Cl. ....................................... 514/567; 514/619

(58) Field of Classification Search ........................ None
See application file for complete search history.

(56) References Cited

U.S. PATENT DOCUMENTS 6,583,128 B2 * 6/2003 Ekwuribe et al. ............. 514/150
2006/0270635 A1  11/2006 Wallace et al.

FOREIGN PATENT DOCUMENTS

| WO | WO-2005/072113 A2 | 8/2005 |
| WO | WO-2007/010514 A2 | 1/2007 |
| WO | WO-2007/010516 A2 | 1/2007 |

OTHER PUBLICATIONS

O'Mahony et al., Postgraduate Medical Journal, (Mar. 1990), 66(773), pp. 238-241.*
Husova, Libuse, et al., "Hepatopathy, coeliac disease and lymphocytic colitis", Ceska A Slovenska Gastroenterologie A Hepatologie—Czech and Slovak Gastroenterology and Hepatology, Ceska Lekarska Spolecnost J.E. Purkyne, Prague, CZ, vol. 61, No. 6, Jan. 1, 2007, pp. 309-313, XP008105161.
Strack, Eberhard, "International Search Report" for PCT/EP2008/068265 as mailed Aug. 11, 2009, 6 pages.

* cited by examiner

*Primary Examiner* — Phyllis G. Spivack
(74) *Attorney, Agent, or Firm* — Pearl Cohen Zedek Latzer, LLP (57) ABSTRACT

The present invention relates to amino-salicylic-aminophenyl compounds for use in the treatment of the inflammatory component of celiac disease. These compounds act by blocking the cytokines released in celiac disease and are specifically useful in the treatment of refractory cases.

2 Claims, 8 Drawing Sheets

COMPOUNDS FOR THE SELECTIVE TREATMENT OF THE INTESTINAL IMMUNO-INFLAMMATORY COMPONENT OF THE CELIAC DISEASE

FIELD OF THE INVENTION

The present invention relates to compounds for the selective treatment of the intestinal immune-inflammatory component of the celiac disease.

The present invention takes origin from the field of drugs for the treatment of diseases having an inflammatory component and localised at the level of the mucosa of the first tract of the small intestine, such as the celiac disease.

BACKGROUND OF THE INVENTION

In particular, the present invention relates to a group of molecules suitable for selectively reducing the inflammation that develops at the level of the duodenum and of the proximal jejunum in individuals suffering from the celiac disease.

The celiac disease, also known as celiac sprue, is a quite common autoimmune disease having genetic, immunological and environmental components.

At the basis of the celiac disease is a permanent intolerance to gliadin, a protein fraction of gluten contained in wheat, or to similar protein fractions soluble in alcohol (prolamines), contained in barley, rye, spelt, kamut and in other minor cereals.

In the celiac disease, the mucosa of the small intestine becomes damaged subsequent to the exposure to the antigen (gliadin). In the disease, the intestinal villi tend to become flattened and the crypts hyper-proliferate for compensation, the enterocytes take up a cubic rather than cylindrical shape and the number of lymphocytes in the intestinal lumen increases.

The symptomatology that accompanies the disease is very complex and not limited to the gastroenteric area. In fact, the typical symptoms at a local level that commonly comprise diarrhoea, abdominal ache with possible bleeding, lactose intolerance, are accompanied by an extra-intestinal symptomatology that may comprise aphthous stomatitis, bone pain, progressive weight loss with weakening. Moreover, in the cases of untreated or refractory celiac disease, there are risks of developing gastrointestinal lymphoma or carcinoma as well.

Not infrequently, moreover, the celiac disease subject may exhibit a deficit of iron or ferritin, along with possible deficiency of vitamins A, B12, D, E, K and folic acid, caused by the intestinal malabsorption. Moreover, the continuous loss of fats through defecation may cause a calcium deficiency and develop two possible complications, one at a renal level with formation of calcium oxalate calculi and the other at a bone level, with the development of osteomalacia, a pathology that causes bone weakening.

In a percentage of individuals, the disease may even be totally or partially asymptomatic, that is, exhibit no clear symptoms or be in a latent form, ready to break out following particular events.

Since the antigen that triggers the disease is known, it is possible to obtain a full remission of the correlated symptoms by simply avoiding the intake of gluten-containing food.

Since the disease control is based on the adherence to a strict diet, it is not sufficient to avoid the intake of food that as everybody knows contains gluten, such as pasta, bread, barley, spelt, but it is also essential to avoid taking food that may contain it in small amounts, for example as a thickening or structuring agent, or as traces lost in the processing.

For example, the celiac disease patient must avoid taking espresso coffee at the bar (this may be contaminated with barley), spices, icing sugar, some pharmaceutical preparations and pay attention also to the glue found, for example, in stamps and mail envelopes.

The diet of celiac disease patients can, in any case, be sufficiently varied and well balanced eating only food such as rice, corn, buckwheat, millet, amaranthus, meat, fish, vegetables, fruit, cheese and legumes.

According to some recent studies there is a critical threshold of 20 ppm gluten per food, beyond which the food contents becomes toxic for the celiac disease subject. The Codex Alimentarius envisages two types of thresholds for labelling food as gluten-free. A first one is set at 100 ppm and relates to "detoxified" food that among the starting materials also contains toxic cereal derivatives, such as for example wheat starch, and a 20 ppm threshold for food free from ingredients derived from toxic cereals.

The strict observance of the diet and of some basic behaviour rules prevents the onset of new symptoms and generally causes, in a more or less marked manner according to the individual response, the remission of the symptoms developed. The diet, however, must be observed for the entire life despite the lack of symptoms or even the lack of antibodies in serum.

Besides the diet, however, no form of treatment is currently available for celiac disease subjects, in particular there are no products that may restrain the inflammatory symptoms that accompany the ingestion, even accidental, of gluten-containing food.

The few methods of therapeutic intervention attempted so far did not lead to the achievement of significant results.

Since the disease is strictly correlated to some genes that code for the antigens of human leukocytes (HLA) DQ2 and DQ8, some forms of treatments aimed at inhibiting the bond of the peptides of gluten at HLA DQ2/DQ8. In particular, some HLA-DQ2-blocking compounds have been tested but without achieving significant results.

The use of zonulin antagonists, a protein involved in the regulation of the intercellular junctions of the small intestine, the expression whereof increases during the acute stage of the disease, has been described in literature for the treatment of the celiac syndrome. However, no drug based on this protein is currently available on the market.

Moreover, anti-inflammatory drugs for topical mucosal use have found no application to date other than the treatment of chronic intestinal inflammatory forms, localised at the level of the colon, the distal tract of the intestine. For this reason, the preparations available on the market for treating the Crohn disease and the ulcerative colitis are sold as suppositories or solutions for rectal use. On the contrary, when these preparations are intended for oral administration, they are formulated for the delayed release of the active principle so as to pass intact along the digestive tube and allow the release of the active principle at the level of the colon only.

These drugs therefore have no effect on the duodenal portion of the intestine where the inflammatory focus in the celiac disease is localised.

Therefore, a clinical need is currently felt of having substances provided with pharmacological activity which should allow restraining the immuno-inflammatory based symptoms that develop at the level of the duodenal mucosa of the small intestine in the celiac disease.

SUMMARY OF THE INVENTION

A general object of the present invention consists in providing new suitable indications on the use of compounds provided with a pharmacological activity.

One of the main objects of the present invention therefore is to provide compounds provided with a selective action on the local immuno-inflammatory component of the celiac disease.

In view of these objects, according to a general aspect of the present invention, compounds are provided having the following common chemical structure (A)

where R1 and R2 are defined hereinafter and X is selected between wherein Y, Z and R3 are defined hereinafter, for the use in the selective treatment of the inflammatory component of the celiac disease.

In one aspect, Applicant has found that compounds of formula (A) and those having the formulae (I) and (II) described herein below, have specific affinity and for example are agonist for the PPARgamma (PPARγ) receptors and provide activation thereof. In particular, the presence of such a receptor has been detected at level of the duodenal epithelial cells in patients affected by the celiac disease, where the anti-inflammatory effect of the compounds of formulae (A), I, and II was demonstrated by a reduction of the production of inflammatory cytokines.

Typically, the compound of formula (I) and (II) have aminophenylpropyonic and amino-salycilic like structure, respectively, and act by blocking the cytokines released in the celiac disease.

In one embodiment, the compounds of formulae (I) and (II) are specifically useful in the treatment of celiac disease refractory to the diet, in dietary errors and in the reduction of the celiac disease remission time.

According to an aspect of the present invention there is provided the use of a compound of formula (I)

(I)

wherein

R1 and R2, equal or different from each other, are selected from the group comprising —H or a linear or branched alkyl group having 1 to 6 carbons, or together they form an aromatic or aliphatic ring with 5 or 6 atoms, Y and Z, equal or different from each other, are selected from the group comprising —H, —OH, —COOH, —OR3, —CH(OR3)COOH, wherein R3 is selected from H, phenyl, benzyl, —CF$_3$, —CF$_2$CF$_3$, vinyl, allyl, a linear or branched alkyl group having 1 to 6 carbons, preferably 3 or 6 C, or mixtures thereof and pharmaceutically acceptable salts or esters, for manufacturing a medicament for selectively treating the immuno-inflammatory component of the celiac disease.

In one embodiment, in the compound of formula (I)

R1 and R2, equal or different from each other, are selected from the group comprising —H or a linear or branched alkyl group having 1 to 6 carbons, and preferably 1 to 3 C Y and Z, equal or different from each other, are selected from the group comprising —H, —OH, —COOH, —OR3, —CH(OR3)COOH, wherein R3 is selected from H, a linear or branched alkyl group having 1 to 6 carbons, preferably 3 to 6 C.

BRIEF DESCRIPTION OF THE DRAWINGS

Embodiments of the invention are illustrated by way of example and not limitation in the figures of the accompanying drawings and in which.

DETAILED DESCRIPTION OF THE INVENTION

By way of an example, the compounds H to Q illustrated in Example 7 and also (±)-2-hydroxy-3-(3'-aminophenyl) propionic acid
(±)-2-methoxy-2-(4'-aminophenyl)acetic acid
(±)-2-ethoxy-2-(3'-aminophenyl)acetic acid
(±)-2-ethoxy-2-(4'-aminophenyl)acetic acid
(±)-2-methoxy-3-(4'-aminophenyl) propionic acid
(±)-2-ethoxy-3-(4'-aminophenyl) propionic acid
(±)-2-ethoxy-3-(3'-aminophenyl) propionic acid.

are suitable for the uses according to the present invention, with particular reference to priopionic acid derivatives.

In one aspect, further examples of the compounds of formula (I) suitable for the uses of the invention, are described in the application WO 2007/010516 whose content is hereby fully incorporated by reference.

According to another aspect of the invention there is provided the use of a compound of formula (II)

(II)

wherein

R1 and R2, equal or different from each other, are selected from the group comprising H, —CO—CH3, —CnH2n−1 wherein n is an integer from 1 to 6, preferably 1 to 3, a linear or branched alkyl group having 1 to 6 carbons, preferably 1 to 3, or together they form an aromatic or aliphatic ring with 5 or 6 atoms;

R3 is selected from H, —CO—CH3, —NHOH, —OH, —OR6, wherein R6 is a linear or branched alkyl group having 1 to 6 carbons;

R4 is selected from H, a linear or branched alkyl group having 1 to 6 carbons; R5, R7, R8 are H atoms;

or

R3 and R4, R4 and R5, or R7 and R8 together form a ring, fused to the benzene ring, either aromatic or aliphatic with 5 or 6 atoms comprising 1 to 2 heteroatoms independently selected from the group consisting of N, O, or mixtures thereof and pharmaceutically acceptable salts or esters, for manufacturing a medicament for selectively treating the immuno-inflammatory component of the celiac disease.

By way of an example the compounds A to G illustrated in example 5 are suitable for uses of the invention.

Further examples of the compounds of formula (II) suitable for the uses of the invention, are described in the application WO 2007/010514 whose content is hereby fully incorporated by reference.

The Applicant has noted that the compounds of formula I and II have a specific activity on the immuno-inflammatory component observed at the level of the intestinal mucosa, in particular at the level of the second duodenal portion, of the celiac disease subject.

The Applicant has further noted that the local anti-inflammatory activity exerted by the compounds of formula (I) and (II) is referable to an inhibitory activity on the release of cytokines, substances that have an important role in phlogistic processes and/or their becoming chronic.

In particular, it has been surprisingly found that the compounds of formula I and II block in a substantial manner, or in any case substantially and significantly inhibit the cytokines in celiac disease subjects only, whereas they do not have a significant activity in subjects suffering from inflammatory diseases affecting a specific gastrointestinal tract, other than the celiac disease.

In particular, the compounds of formula I and II are suitable for blocking the so-called prophlogogen Th1 (T helper cell type 1) cytokines since they favour the recruitment of immune and inflammatory cells at the lesion site.

This specific activity may be ascribed to the fact that in the celiac disease the persistence of a type Th1 phlogosis reflects the activation of the immune system against the antigen (gliadin fraction of gluten) that cannot be eliminated and towards which the system is not capable of developing tolerance.

Typical prophlogogen cytokines (Th1) involved in the immunopathogenesis of the celiac disease comprise (L-1, IL-2, IL-6 (interleukins 1, 2, 6), IFN (interferon). Moreover, the cytokines associated to Th2 (T helper cell type 2), as well as the cytokines derived from macrophages such as TNF-α (tumor necrosis factor) are also involved in the celiac disease. In particular, the TNF-α has an important role in the development of chronic inflammatory diseases due to its ability to boost the production of prophlogogen cytokines, some of which are provided with considerable toxicity.

In particular, the effect of the compounds of formula (I) and (II) on the production and release of cytokines from intestinal mucosa samples suffering from the celiac disease has been verified using an organic culture system. In particular, an effective reduction of phlogosis has been noted, as highlighted by a significant reduction of the IFN-γ, IL-2, TNF-α values using one or more of the compounds of formula (I) (II) in biopsies of intestinal mucosa subject to culture.

According to another aspect of the invention, there is provided the use of a compound of formula I or II and mixtures thereof, as described before, for the manufacture of a medicament for treating the inflammation in refractory celiac disease subjects.

According to another aspect of the invention, there is provided the use of a compound of formula I or II and mixtures thereof, as described before, for the manufacture of a medicament for treating an inflammatory reaction in a celiac disease subject on a diet, triggered by a dietary error.

According to another aspect of the invention, there is provided the use of a compound of formula I or II and mixtures thereof, for the manufacture of a medicament, typically, in combination with one or more pharmaceutically acceptable excipients or adjuvants, for treating the immuno-inflammatory component in the celiac disease for shortening the clinical and/or histological remission time.

In preparing medicaments according to one or more of the aspects of the invention it is also possible to use, in addition to one or more pharmaceutically acceptable excipients, also lubricants, humectants, suspending agents, dispersing agents, preservatives typically used within the scope of preparations for pharmaceutical use.

In one embodiment the compounds of formula (I) and/or (II) can be administered in various forms such as tablets, capsules, granular formulations, dispersions and other formulation typical of the pharmaceutical field.

Typically, the active ingredients (I) and (II) can be incorporated in the formulation suitable for the administration in an amount effective to achieve the antiinflammatory response in the celiac disease.

By way of an example, the active ingredient can be incorporated in the pharmaceutical composition in an amount ranging from 50 mg to 2000 mg, preferably in the range from 200 to 600 mg, more preferably from 250 to 500 mg.

It has been shown that the use of medicaments based on one or more compounds of formula (I) and/or (II) determines an improvement of compliance and of patient and doctor, decreasing the remission time.

In another embodiment, the compounds of formula (I) and/or (II) found further therapeutic application in the treatment of resistant and/or refractory celiac disease.

The following examples are given merely as an illustration of the present invention, and are not to be intended as limiting the scope of protection as it appears from the annexed claims.

Example 1

The effect of mesalazine, one of the preferred compound of the invention, on the inflammatory component observed in the celiac disease, was evaluated.

To this end, 16 subjects in the active stage of the disease and 6 patients in clinical remission stage on a gluten-free diet were selected.

5 biopsy fragments per each study subject were taken by EGDS examination.

Each fragment of intestinal mucosa was placed in culture in a suitable medium, both with and without Mesalazine (5ASA).

The following was then observed in culture liquids:

the level of cytokines released in the different culture media the amount of the same cytokines present in the suitably homogenised biopsy mucosa.

Materials and Methods

Method 3 groups of subjects were evaluated.

The first (atrophic) group included 29 subjects with serum tests positive to antiendomysium and anti-transglutaminase antibodies, with a neo-diagnosis of celiac disease and gluten-containing diet.

The second (Remission) group included 17 celiac disease subjects in clinical remission and gluten-free diet for at least 6 months.

The third (Healthy) group included subjects not suffering from the celiac disease but suffering from inflammation of the gastro-enteric tract.

Cytokine Assay in Culture Liquids

Organ Cultures:

The study patients were subject to 5 biopsies of duodenal mucosa by EGDS examination: one for the histological assay and the other four (each divided into two parts) subject to culture respectively with one culture medium only (Medium C) and with gliadin peptide, and with culture medium with gliadin in the presence of mesalazine (Medium+5ASA C).

The biopsies were washed in saline for two minutes at least three times. The biopsies were placed in culture media having a volume equal to 1 ml:

MEDIUM (RPM11860+Fetal calf serum+Penicillin/Streptomycin)

MEDIUM+peptic-tryptic digest of gliadin or 31-43 or other cereals

MEDIUM+Mesalazine (5-ASA)

MEDIUM+peptic-tryptic digest of gliadin +5-ASA (1.5-8.0 mg per ml of medium)

The biopsies are incubated in an O2 (95%) and CO2 (5%) atmosphere at a temperature of 37° C. for a period ranging from 4 h to 72 h.

Three different amounts of medium are shared for the ELISA assay of Th1 and Th2 cytokines released in culture media.

Cytokine Assay from Homogenate

After an incubation time ranging from 4 h to 72 h, at a T of 37° C.:

The bioptic fragment is washed three times in saline for two minutes

The biopsies are homogenised by mechanical or chemical disintegration

Centrifugation is carried out, the supernatant is collected and transferred in a 1.5 ml Eppendorf Fixed cytokines in the mucosal tissue are assayed by the Elisa assay.

Results

The data found show that the presence of Mesalazine in culture media blocks the cytokines in celiac disease subjects only, thus selectively determining a reduction of the inflammatory component in samples taken from celiac disease subjects (Table 1).

TABLE 1

Medium C/Medium + SASA. C

| Population | Cytokine | Parameter | N | Mean | Std Dev | Std Error | Min | Median | Max | Wilcoxon signed Rank Test |
|---|---|---|---|---|---|---|---|---|---|---|
| Atrophic | IFN | Medium C | 22 | 0.196 | 0.197 | 0.0420 | 0.0450 | 0.119 | 0.916 | p = 0.08 |
| | | Medium + 5ASA C | 22 | 0.136 | 0.165 | 0.0351 | 0.0330 | O.0670 | 0.780 | |
| | | Difference | 22 | 0.0601 | 0.250 | 0.0533 | −0.549 | 0.0260 | 0.877 | |
| | IL-2 | Medium C | 15 | 0.175 | 0.136 | 0.0351 | 0.0100 | 0.161 | 0.569 | p = 0.03 |
| | | Medium + 5ASA C | 15 | 0.119 | 0.0978 | 0.0252 | 0.0130 | 0.0910 | 0.355 | |
| | | Difference | 15 | 0.0559 | 0.0S57 | 0.0221 | −0.060 | 0.0490 | 0.258 | |
| | TNF | Medium C | 21 | 0.477 | 0.585 | 0.128 | 0.0550 | 0.174 | 2.077 | p = N.S. |
| | | Medium + 5ASA C | 21 | 0.472 | 0.651 | 0.142 | 0.0590 | 0.204 | 2.134 | |
| | | Difference | 21 | 0.0048 | 0.447 | 0.0974 | −1.398 | 0.0150 | 0.972 | |
| Remission | IFN | Medium C | 15 | 0.240 | 0.154 | 0.0398 | 0.0610 | 0.209 | 0.534 | p = N.S. |
| | | Medium + 5ASA C | 15 | 0.201 | 0.I35 | 0.0348 | 0.0390 | 0.208 | 0.429 | |
| | | Difference | 15 | 0.0383 | 0.123 | 0.0317 | 0.262 | 0.0500 | 0.209 | |
| | IL-2 | Medium C | 12 | 0.315 | 0.176 | 0.0509 | 0.0420 | 0.284 | 0.732 | p = N.S. |
| | | Medium + 5ASA C | 12 | 0.309 | 0.223 | 0.0644 | 0.0500 | 0.253 | 0.737 | |
| | | Difference | 12 | 0.0061 | 0.147 | 0.0425 | 0.314 | 5E-4 | 0.201 | |
| | TNF | Medium C | 15 | 0.948 | 0.796 | 0.206 | 0.0830 | 0.578 | 2.477 | p = N.S. |
| | | Medium + 5ASA C | 15 | 0.894 | 0.689 | 0.178 | 0.249 | 0.571 | 2.301 | |
| | | Difference | 15 | 0.0541 | 0.297 | 0.0767 | 0.460 | 0.0790 | 0.728 | |
| Positive control | IFN | Medium C | 7 | 0.145 | 0.0643 | 0.0243 | 0.1D2 | 0.112 | 0.281 | p = N.S. |
| | | Medium + 5ASA C | 7 | 0.149 | 0.0480 | 0.0182 | 0.111 | 0.140 | 0.252 | |
| | | Difference | 7 | 0.004 | 0.0398 | 0.0150 | 0.047 | 0.029 | 0.0510 | |
| | IL-2 | Medium C | 7 | 0.532 | 0.171 | 0.0659 | 0.223 | 0.S35 | 0.730 | p = 0.07 |
| | | Medium + 5ASA C | 7 | 0.356 | 0.140 | 0.0530 | 0.169 | 0.379 | 0.529 | |
| | | Difference | 7 | 0.116 | 0.169 | 0.0638 | −0.028 | 0.247 | 0.351 | |
| | TNF | Medium C | 7 | 0.253 | 0.129 | 0.0486 | 0.105 | 0.220 | 0.489 | p = N.S, |
| | | Medium + 5ASA C | 7 | 0.259 | 0.105 | 0.0397 | 0.127 | 0.229 | 0.434 | |
| | | Difference | 7 | 0.005 | 0.201 | 0.0761 | 0.260 | 0.0040 | 0.362 | |

TABLE 2

PT C/PT + 5ASA C

| Population | Cytokine | Parameter | N | Mean | Std Dev | Std Error | Min | Median | Max | Wilcoxon Signed Rank Test |
|---|---|---|---|---|---|---|---|---|---|---|
| Atrophic | IFN | PT C | 22 | 0.211 | 0.213 | 0.0454 | 0.0400 | 0.126 | 0.849 | p = 0.05 |
| | | PT + 5ASA C | 22 | 0.145 | 0.195 | 0.0416 | 0.0270 | 0.0545 | 0.816 | |
| | | Difference | 22 | 0.0657 | 0.178 | 0.0379 | −0.244 | 0.0505 | 0.563 | |
| | IL-2 | PT C | 15 | 0.151 | 0.124 | 0.0320 | 0.0100 | 0.124 | 0.507 | p = 0.012 |
| | | PT + 5ASA C | 15 | 0.124 | 0.137 | 0.0355 | 0.0070 | 0.0770 | 0.440 | |
| | | Difference | 15 | 0.0270 | 0.0749 | 0.0193 | −0.217 | 0.0410 | 0.0900 | |
| | TNF | PT C | 21 | 0.600 | 0.788 | 0.172 | 0.0550 | 0.200 | 2.725 | p < 0.0001 |
| | | PT + 5ASA C | 21 | 0.414 | 0.584 | 0.127 | 0.0700 | 0.120 | 2.163 | |
| | | Difference | 21 | 0.187 | 0.272 | 0.0593 | −0.052 | 0.0580 | 0.986 | |
| Remission | IFN | PT C | 15 | 0.254 | 0.210 | 0.0543 | 0.0560 | 0.185 | 0.870 | p = 0.022 |
| | | PT + 5ASA C | 15 | 0.153 | 0.120 | 0.0309 | 0.0370 | 0.0960 | 0.387 | |
| | | Difference | 15 | 0.101 | 0.210 | 0.0541 | −0.060 | 0.0210 | 0.791 | |
| | IL-2 | PT C | 12 | 0.271 | 0.218 | 0.0630 | 0.0360 | 0.204 | 0.815 | p = N.S. |
| | | PT + 5ASA C | 12 | 0.234 | 0.126 | 0.0363 | 0.0650 | 0.194 | 0.473 | |
| | | Difference | 12 | 0.0365 | 0.141 | 0.0425 | −0.187 | 0.0260 | 0.342 | |
| | TNF | PT C | 15 | 0.996 | 0.832 | 0.215 | 0.216 | 0.673 | 2.951 | p = 0.005 |
| | | PT + 5ASA C | 15 | 0.305 | 0.708 | 0.183 | 0.151 | 0.545 | 2.294 | |
| | | Difference | 15 | 0.191 | 0.221 | 0.05S9 | −0.188 | 0.221 | 0.657 | |
| Positive control | IFN | PT C | 7 | 0.141 | 0.0766 | 0.0289 | 0.0700 | 0.124 | 0.295 | p = N.S. |
| | | PT + 5ASA C | 7 | 0.116 | 0.0628 | 0.0237 | 0.0540 | 0.121 | 0.210 | |
| | | Differenza | 7 | 0.0247 | 0.0505 | 0.0191 | −0.030 | 0.0090 | 0.105 | |
| | IL-2 | PT C | 7 | 0.501 | 0.243 | 0.0920 | 0.284 | 0.469 | 0.996 | p = N.S. |
| | | PT + 5ASA C | 7 | 0.521 | 0.259 | 0.0979 | 0.191 | 0.468 | 0.951 | |
| | | Difference | 7 | −0.020 | 0.123 | 0.0465 | −0.184 | 0.0210 | 0.144 | |
| | TNF | PT C | 7 | 0.313 | 0.133 | 0.0504 | 0.183 | 0.280 | 0.511 | p = N.S. |
| | | PT + 5ASA C | 7 | 0.291 | 0.127 | 0.0479 | 0.159 | 0.274 | 0.470 | |
| | | Difference | 7 | 0.0226 | 0.102 | 0.0385 | −0.190 | 0.0250 | 0.110 | |

TABLE 3

Medium O/Medium + 5ASA O

| Population | Cytokine | Parameter | N | Mean | Std Dev | Std Error | Min | Median | Max | Wilcoxon Signed Rank Test |
|---|---|---|---|---|---|---|---|---|---|---|
| Atrophic | IFN | Medium 0 | 9 | 0.277 | 0.0561 | 0.0187 | 0.212 | 0.274 | 0.361 | p = 0.003 |
| | | Medium + 5ASA | 9 | 0.202 | 0.0585 | 0.0195 | 0.125 | 0.193 | 0.311 | |
| | | Difference | 9 | 0.0951 | 0.0594 | 0.0198 | 0.0270 | 0.0560 | 0.227 | |
| | IL-2 | Medium 0 | 0 | | | | | | | |
| | | Medium + 5ASA | 0 | | | | | | | |
| | | Difference | 0 | | | | | | | |
| | TNF | Medium 0 | 11 | 0.138 | 0.0546 | 0.0165 | 0.0710 | 0.115 | 0.233 | p = N.S. |
| | | Medium + 5ASA | 11 | 0.123 | 0.0395 | 0.0119 | 0.0660 | 0.106 | 0.174 | |
| | | Difference | 11 | 0.0154 | 0.0297 | 0.0089 | −0.035 | 0.0100 | 0.0640 | |
| Remission | IFN | Medium 0 | 4 | 0.252 | 0.0748 | 0.0374 | 0.183 | 0.251 | 0.324 | p = N.S. |
| | | Medium + 5ASA | 4 | 0.133 | 0.0577 | 0.0289 | 0.0490 | 0.151 | 0.174 | |
| | | Difference | 4 | 0.120 | 0.0505 | 0.0252 | 0.0440 | 0.142 | 0.150 | |
| | IL-2 | Medium 0 | 0 | | | | | | | |
| | | Medium + 5ASA | 0 | | | | | | | |
| | | Difference | 0 | | | | | | | |
| | TNF | Medium 0 | 5 | 0.122 | 0.0331 | 0.0118 | 0.0800 | 0.133 | 0.159 | p = N.S. |
| | | Medium + 5ASA | 5 | 0.122 | 0.0230 | 0.0103 | 0.0960 | 0.114 | 0.154 | |
| | | Difference | 5 | −0.00 | 0.0371 | 0.0169 | −0.057 | 0.0050 | 0.0370 | |
| Positive control | IFN | Medium 0 | 0 | | | | | | | |
| | | Medium + 5ASA | 0 | | | | | | | |
| | | Difference | 0 | | | | | | | |
| | IL-2 | Medium 0 | 0 | | | | | | | |
| | | Medium + 5ASA | 0 | | | | | | | |
| | | Difference | 0 | | | | | | | |
| | TNF | Medium 0 | 0 | | | | | | | |
| | | Medium + 5ASA | 0 | | | | | | | |
| | | Difference | 0 | | | | | | | |

TABLE 4

| Population | Cytokine | Parameter | N | Mean | Std Dev | Std Error | Min | Median | Max | Wilcoxon Signed Rank Test |
|---|---|---|---|---|---|---|---|---|---|---|
| Atrophic | IFN | PT 0 | 9 | 0.223 | 0.0496 | 0.0165 | 0.151 | 0.223 | 0.287 | p = 0.019 |
| | | PT + 5ASA 0 | 9 | 0.179 | 0.0589 | 0.0196 | 0.100 | 0.193 | 0.243 | |
| | | Difference | 9 | 0.0437 | 0.0409 | 0.0136 | −0.009 | 0.0380 | 0.0980 | |
| | IL-2 | PT 0 | 0 | | | | | | | |
| | | PT + 5ASA 0 | 0 | | | | | | | |
| | | Difference | 0 | | | | | | | |
| | TNF | PT 0 | 11 | 0.156 | 0.0627 | 0.0189 | 0.0680 | 0.134 | 0.254 | p = 0.002 |
| | | PT + 5ASA 0 | 11 | 0.101 | 0.0463 | 0.0140 | 0 | 0.0980 | 0.160 | |
| | | Difference | 11 | 0.0554 | 0.0735 | 0.0222 | −0.004 | 0.0270 | 0.254 | |
| Remission | IFN | PT 0 | 4 | 0.200 | 0.0931 | 0.0466 | 0.120 | 0.172 | 0.334 | p = N.S. |
| | | PT + 5ASA 0 | 4 | 0.177 | 0.0692 | 0.0346 | 0.120 | 0.161 | 0.264 | |
| | | Difference | 4 | 0.0230 | 0.0411 | 0.206 | −0.021 | 0.0215 | 0.0700 | |
| | IL-2 | PT 0 | 0 | | | | | | | |
| | | PT + 5ASA 0 | 0 | | | | | | | |
| | | Difference | 0 | | | | | | | |
| | TNF | PT 0 | 5 | 0.126 | 0.0276 | 0.0123 | 0.0840 | 0.127 | 0.158 | p = N.S. |
| | | PT + 5ASA 0 | 5 | 0.107 | 0.0310 | 0.0139 | 0.0630 | 0.110 | 1480. | |
| | | Difference | 5 | 0.0194 | 0.0089 | 0.0040 | 0.0100 | 0.0210 | 0310 | |
| Positive control | IFN | PT 0 | 0 | | | | | | | |
| | | PT + 5ASA 0 | 0 | | | | | | | |
| | | Difference | 0 | | | | | | | |
| | 11,2 | PT 0 | 0 | | | | | | | |
| | | PT + 5ASA 0 | 0 | | | | | | | |
| | | Difference | 0 | | | | | | | |
| | TNF | PT 0 | 0 | | | | | | | |
| | | PT + 5ASA 0 | 0 | | | | | | | |
| | | Difference | 0 | | | | | | | |

The inflammatory component reduction achieved allows the use of mesalazine alone or as a therapeutic support in all slow or difficult clinical resolution cases.

Example 2

Gene Expression of Cytokines

The bioptic duodenal fragments taken from the patient during the gastroscopy procedure, have been placed in culture at 37° C. for 48 h in the absence and in the presence of the 5-ASA drug. After the culture, the fragments have been homogenized in a single-phase solution composed of phenol and guanidinium (Isol-RNA Lysis Reagent).

A homogenizer IKA T10-Ultra Turrax has been used for the homogenization.

All the insoluble material has been separated from the solution by centrifugation and the supernatant has been transferred to a clean test tube, to which 200 µl of chloroform per ml of Lysis has been added.

After a short mechanical shake, the samples have been left to settle for a few minutes at ambient temperature and later centrifuged at 12000 rpm for 15 minutes at 4° C. The inorganic step containing RNA has been transferred to a clean test tube.

RNA has been made precipitate by adding 500 µl of isopropyl alcohol per ml of Lysis. The samples have been incubated at ambient temperature for 10 minutes and then centrifuged at 12000 rpm for 15 minutes at 4° C.

After having removed the supernatant, the RNA sediment has been washed with 1000 µl of 75% ethanol per ml of Lysis, shaken mechanically and centrifuged at 7500 rpm for 5 minutes at 4° C. Finally, the ethanol has been removed and the RNA sediment has been air-dried under chemical hood.

RNA has been re-suspended in a suitable quantity of RNasi-free water.

The concentration of the RNA has been determined by measuring the absorption at 260 nm at the spectrophotometer; also the ratio A260/A280 for different RNA templates has been valued.

RT-PCR

The cDNA has been synthesized beginning from different quantities of extracted RNA diluted in suitable volumes of RNasi-free water. The cDNA of the genes concerned (cytokines) has been amplified by PCR with the use of specific primers.

Masterscript—RT-PCR System (5 PRIME) has been used for the RT-PCR.

In order to verify the presence and the quantity of mRNA coding for the cytokines in the bioptic samples, a 1% agarose gel electrophoresis in 1×TBE has been executed.

Figure 1:
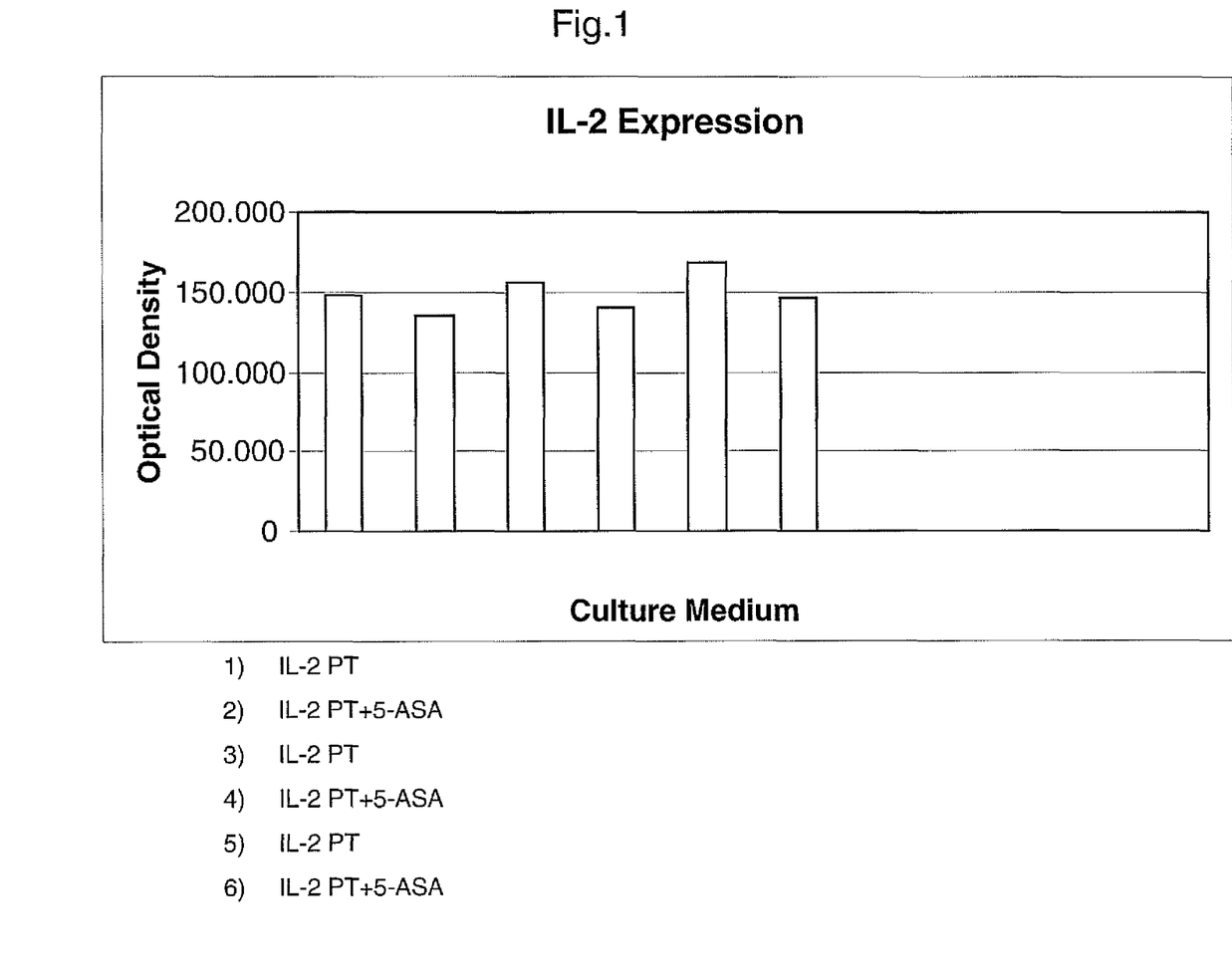
FIG. 1 is a graphical depiction of the results verifying the presence and quantity of mRNA coding for the cytokines in biopic samples taken from a patient during a gastroscopy procedure.

The results obtained are shown in the diagram of FIG. 1.

Example 3

Presence of the PPARgamma Receptor in Duodenal Epithelial Cells of Celiac Disease Patients Peroxisome Proliferator-Activated Peceptor-gamma belongs to the superfamily of nuclear receptors, that includes receptors for estrogens, glucocorticoids, thyroid hormones, vitamin D3 and retinoic acid, as well as receptors capable of bonding different products of lipid metabolism, such as the PPAR and the LXR receptor.

Specifically, the PPAR family includes 3 subtypes (PPAR alpha, beta or delta, and gamma) with different tissue distribution and different ligands specificity.

Both PPAR gamma and alpha have been expressed in differentiated human macrophages, where they regulate the genes implicated in the inflammatory response and modulate the macrophagic differentiation.

Different PPARgamma agonists inhibit the production of inflammatory cytokines in human monocytes and reduce the genes expression for TNF-alpha, IL-6, IL-1b, iNOS, gelatinous B, scavenger receptor A and COX-2 in activated macrophages, confirming the anti-inflammatory role of PPAR-gamma.

One of the main objects was to detect the presence of such a receptor in duodenal epithelial cells of celiac disease patients, where the anti-inflammatory effect of the compounds of formulae (A), I, II and specifically of 5-ASA revealed by a reduction of the production of inflammatory cytokines, has been previously confirmed.

Immunofluorescence

A duodenal bioptic fragment has been taken, by EGDS procedure, both from celiac disease patients on gluten-containing diet and from subjects not affected by celiac disease (control group). The bioptic fragments have been washed, oriented in OCT and stored at −80° C. Some sections of 5 μm have been obtained from each frozen bioptic piece (taken in the EGDS step both from celiac disease patients and from subjects not affected by the disease), such sections have been exposed to the PPARgamma primary antibody overnight (after suitable fixation and specificity elimination treatments).

After having been washed in PBS, the samples were incubated for about one hour with the secondary fluoresceined antibody ALEXA 488. In the case of binding of the primary antibody to the PPARgamma receptor, if present, a primary/secondary antibody complex is formed, revealable as fluorescence on the section, observable by microscope.

Figure 2:
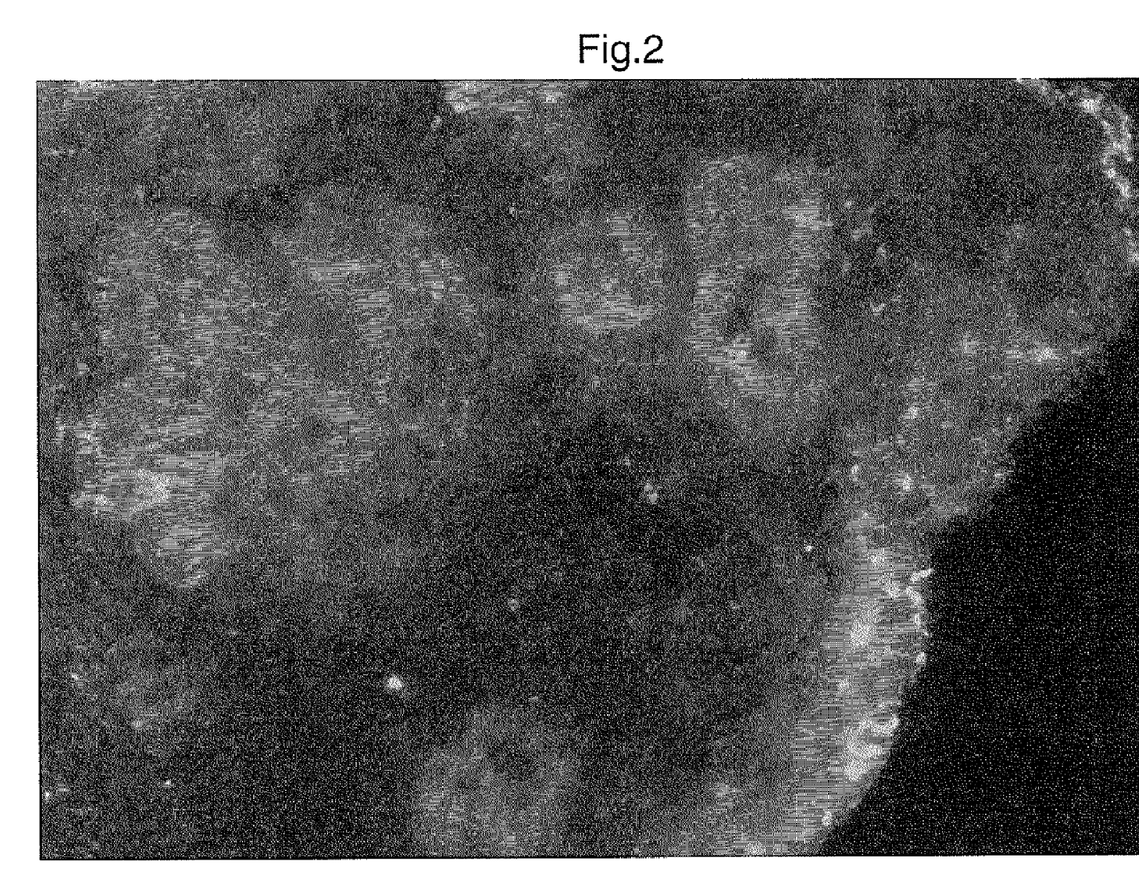
FIGS. 2 and 3 are fluorescence microscope photos showing the presence of the PPARgamma receptor as revealed by the fluorescence signal detectable in the section peripheral portion.
Figure 3:
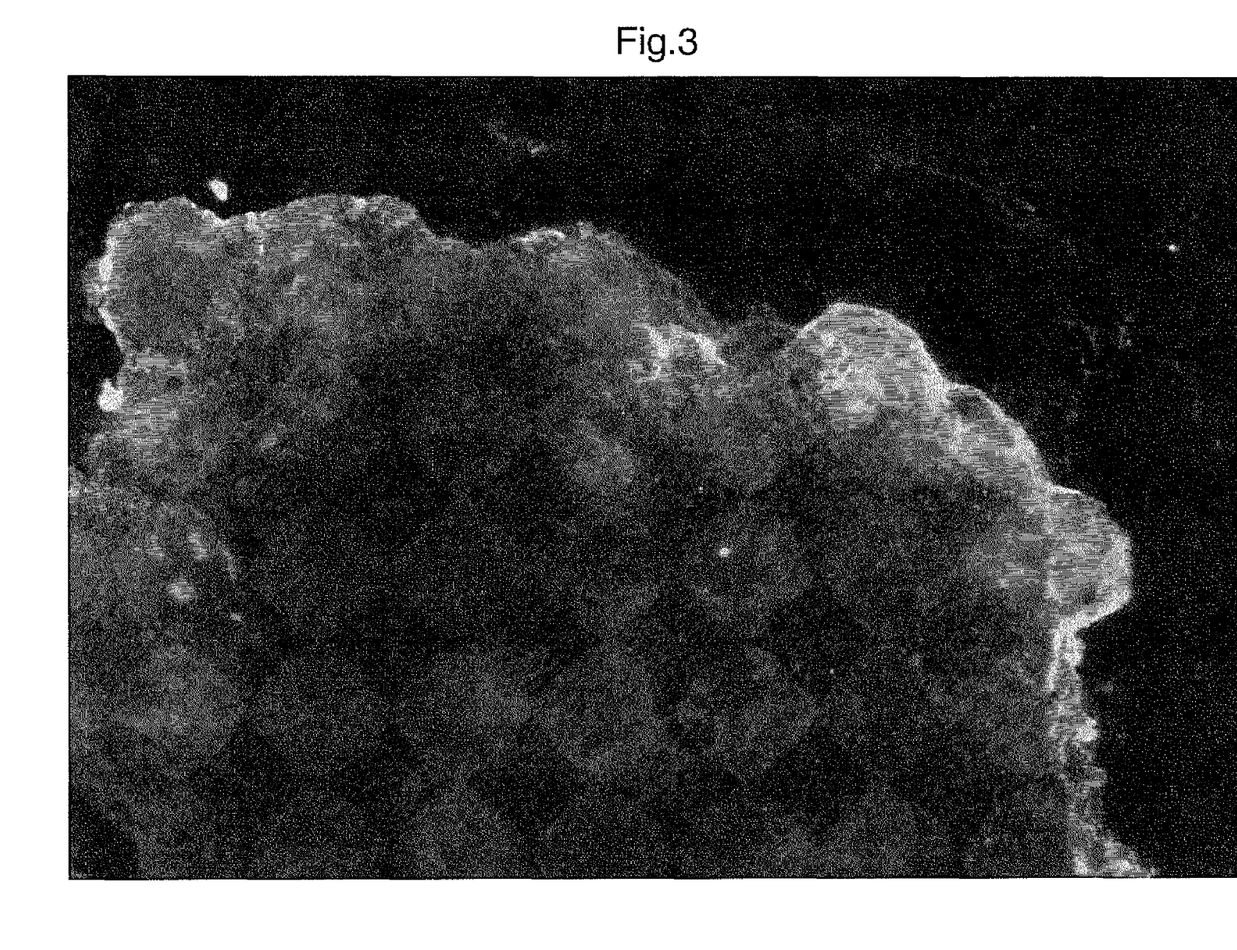

The presence of the PPARgamma receptor, revealed by a fluorescence microscope, is evident from FIGS. 2 and 3 (photos diagnosis).

In particular, in the images of FIGS. 2 and 3 the presence of the receptor is revealed by the fluorescence signal detectable in the section peripheral portion. The fluorescence demonstrates the presence of the PPARgamma at the level of enterocytes, intestinal epithelial cells on the surface turned toward the intestinal lumen.

Figure 4:
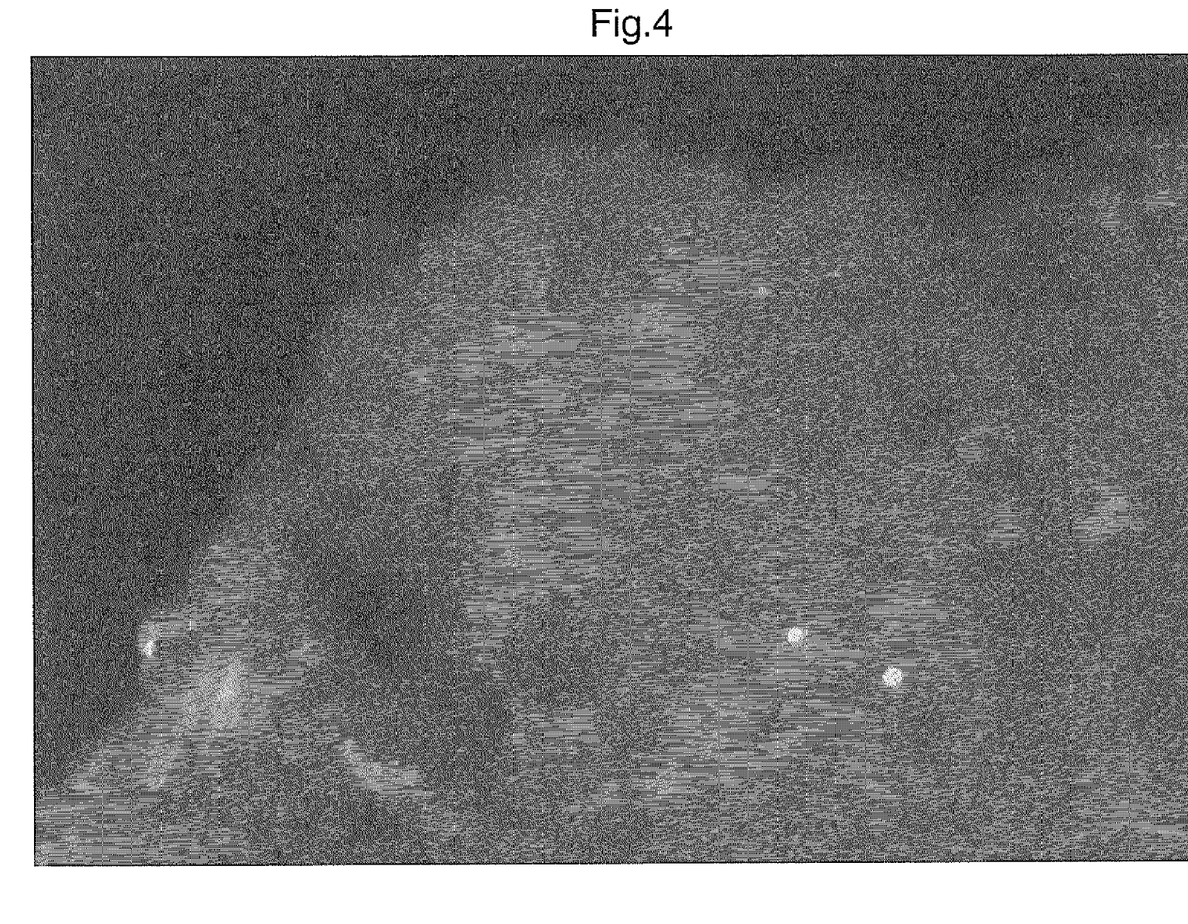
FIGS. 4 and 5 are fluorescence microscope photos showing the absence of fluorescence signal and, consequently, of the receptor of the negative control biopsies of the patients not affected by celiac disease.
Figure 5:
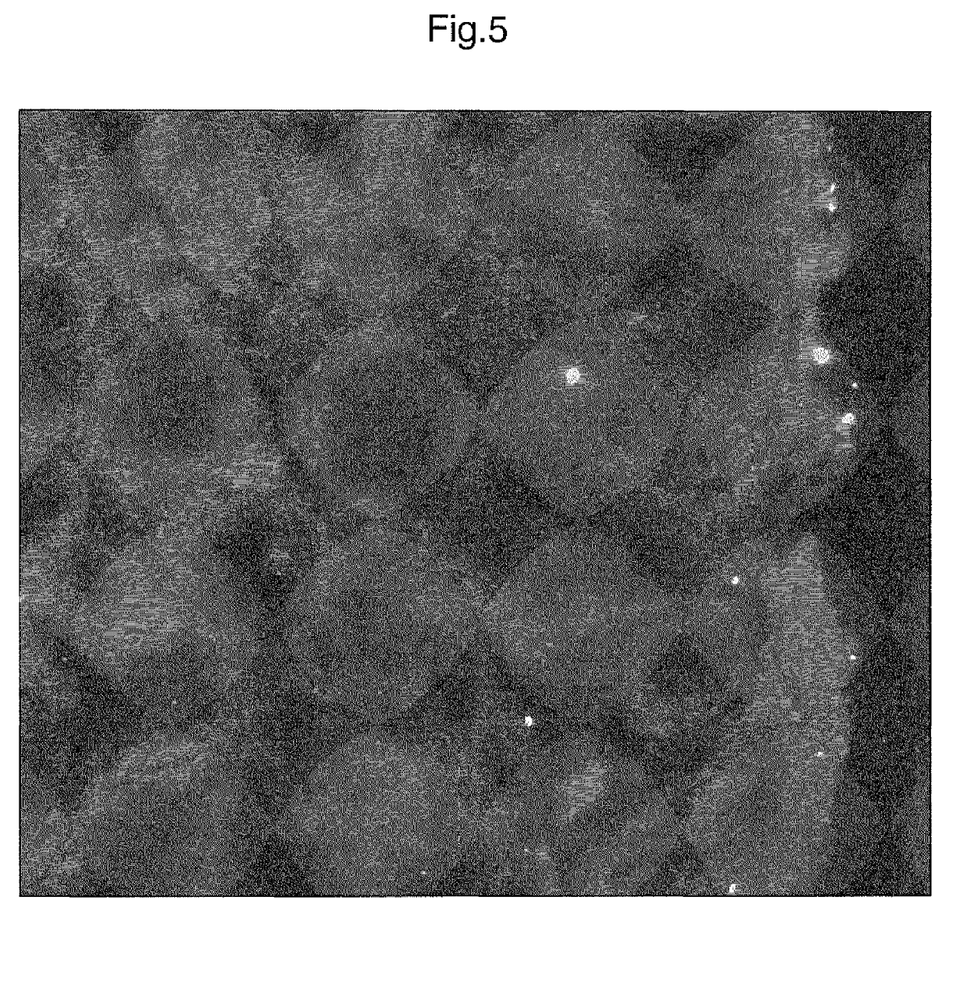

Biopsies of the patients not affected by celiac disease have been used as negative control: the result has been an absence of signal, and consequently, of the receptor absence on the sections analyzed by microscope. In particular, FIGS. 4 and 5 (controls) show that no fluorescence has been detected: this is the sign of the receptor absence, at the level of the same intestinal portion, in the control, healthy group.

In the same way the compounds detailed herein below were tested and similar results were achieved:

Example 4

The gene expression (mRNA) of the pro-inflammatory cytokines IL-2, TFN-alpha and IFN-gamma, released in the disease acute phase, was monitored.

Figure 6:
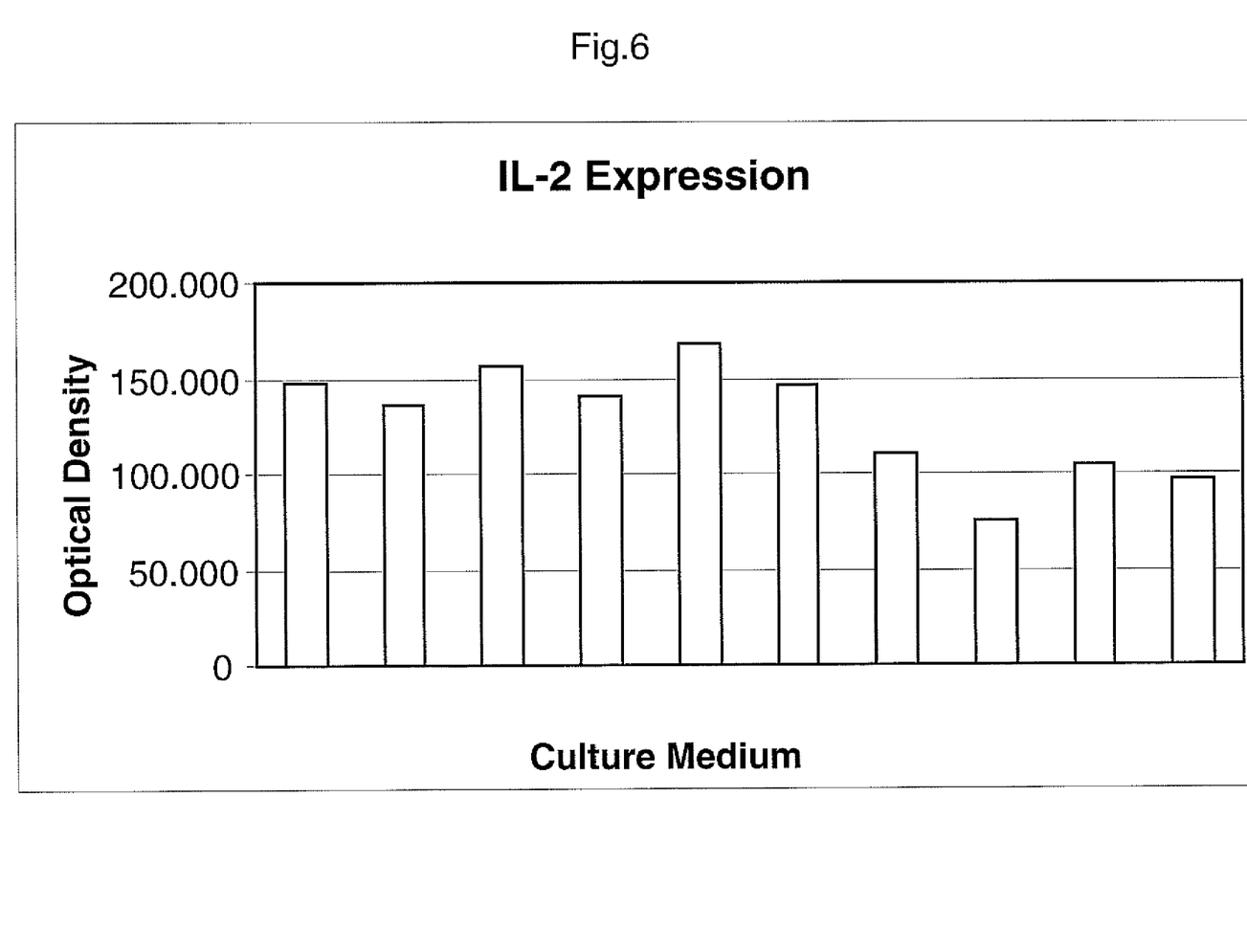
FIGS. 6, 7 and 8 quote the optical density values extrapolated from different bands, obtained by electrophoretic run with 1× agarose gel, related to cytokine amplifiers.
Figure 7:
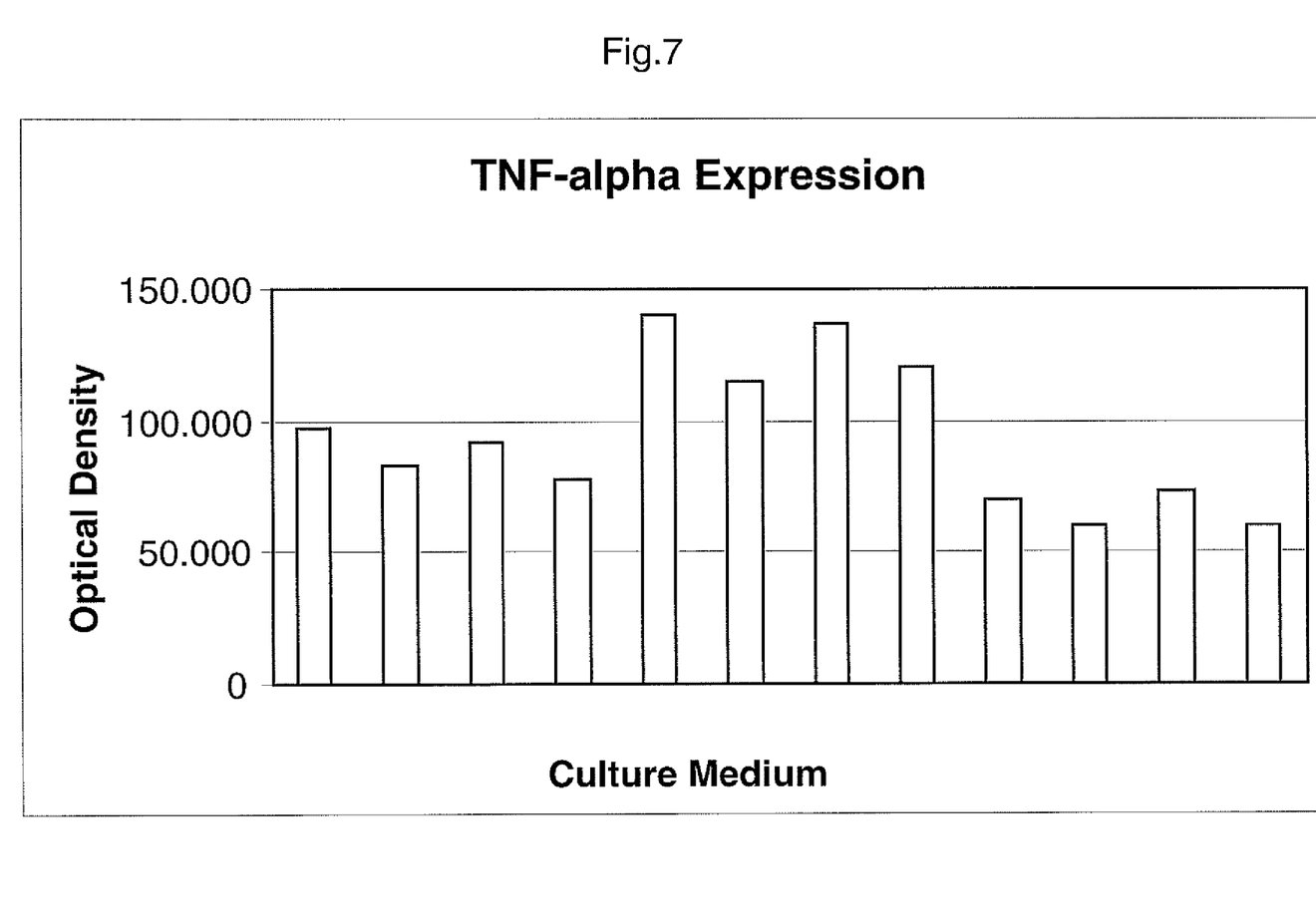
Figure 8:
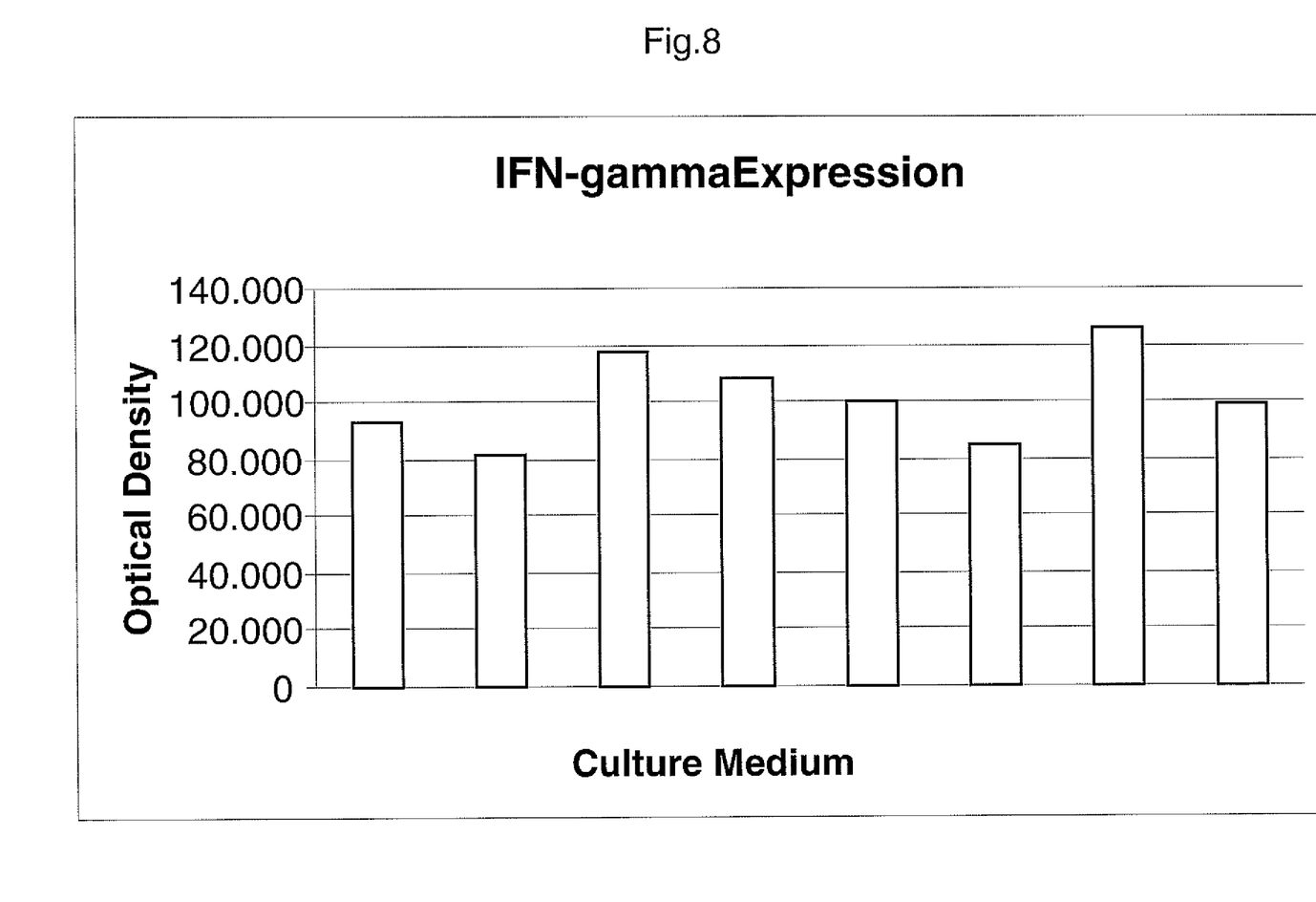

In particular the diagrams illustrated in FIGS. 6 to 8 quote the optical density values (IMAGE J) extrapolated from different bands, obtained by electrophoretic run with 1× agarose gel, related to the cytokine amplifiers subject of the study.

The gene expression of the cytokines has been assessed by RT-PCR of the RNA extracted by duodenal biopsies of the patients affected by celiac disease. Such biopsies have been maintained for growing at 37° C. for 48 h, both in a culture medium containing a tryptic digest of gliadin (PT) and in a PT medium, to which the 5-ASA drug has been added.

Results

The three diagrams show that, in the bioptic fragments kept in culture in the drug presence, the gene expression (mRNA) of the pro-inflammatory cytokines IL-2, TFN-alpha and IFN-gamma, released in the disease acute phase, is well reduced.

The reduction increases when the patient is subjected to a more lasting and constant treatment with the drug.

Example 5

Study on the Effects of Compounds according to the invention on PPARγ Activation/Expression and Regulation of Cell Proliferation and Apoptosis Materials and Methods Compounds A-G 5-ASA was purchased at Sigma-Aldrich™ (St Quentin Fallavier, France). Rosiglitazone was acquired at Spi Bio™ (Massy, France). The following compounds A to G, falling within the formula (II) were tested:

G

Cell Lines

The colon cell line HT-29 STD (ATCC HTB-38) was routinely grown in DMEM supplemented with 10% heat-FCS, and antibiotics. Cells were grown in monolayers, incubated at 37° C. in 5% CO2 and 95% relative humidity.

Transient Transfection with PPARγ and Stimulation of Cells

HT-29 STD cells were transiently transfected using the Effectene™ transfection reagent (Qiagen™) according to instructions from the manufacturer. To test PPARγ activation, we performed transfection with 500 ng of a minimal promoter construct containing two copies of PPRE obtained from the cytochrome p450 4A (2×CYP). The renilla luciferase plasmid (0.1 µg/well) was also transfected as an internal control for monitoring transfection efficiency and for normalizing the firefly luciferase activity. Transfected cells were left for 48 hours incubation at 37° C. Stimulations were performed after incubation of cells during 3-6-9-12-15-18-24 hours with the compounds A-G at a concentration of 30 mM and compared with the two PPARγ synthetic ligands 5-ASA 30 mM and rosiglitazone 10-5 M used as positive controls. The pH of the drug solutions was adjusted to 7.4 with NaOH. Total cell extracts were prepared using the Passive Lysis Buffer (Promega™, Madison, Wis.). Luciferase activity was assayed in 20 µl of the extract using the Promega™ Dual Luciferase assay system according to the manufacturer's protocol. Transfections were assayed in triplicate in at least three separate experiments. The luciferase activity was expressed as fold of the activity obtained in cells treated with the different molecules divided by luciferase activity from non-stimulated cells.

Evaluation of PPARγ and β-Actin by Western Blot Analysis

The total proteins were obtained by cell homogenization in an extraction buffer consisting of PBS with 2% Triton™, Phenyl Methyl Sulphonyl Fluoride (PMSF) 100 mM and a classical protease inhibitor cocktail. The total proteins were then separated by polyacrylamide gel electrophoresis and electroblotted. Polyvinylidendifluoride (PVDF) membranes were incubated overnight with rabbit polyclonal primary antibody directed against PPARγ (dilution 1/500, TEBU, Le Perray en Yveline, France). β-actin was detected using a rabbit monoclonal primary antibody diluted at 1/10,000 (Sigma). Immunodetection with a secondary peroxidase-conjugated antibody (1/1000, Dako™, Trappes, France) and chemiluminescence was performed according to the manufacturer's protocol (ECL™, Amersham Pharmacia Biotech™, Orsay, France). Optical density values of PPARγ were given for each condition in proportion to the quantity of the internal control β-actin in the same sample.

Analysis of Cell Proliferation by Ki-67 Immunostaining

After 24 h of culture, HT-29 STD cells were treated during 24 h with the compounds A, B, C, D and F, at 30 mM. 5-ASA (30 mM) and rosiglitazone (10-5 M) were used as positive controls. The molecule G was not included in this experiment due to its poor solubility. The pH of the drug solutions was adjusted to 7.4 with NaOH. Cells were fixed in PFA 4%, permeabilized in PBS containing 0.1% Triton X-100™ at 4° C. and then incubated with goat normal serum and blocking buffer (1% BSA in PBS) to minimize non-specific adsorption of the antibody.

Cell proliferation was assessed by a nuclear Ki-67 staining using mouse monoclonal primary antibody directed against Ki-67 (dilution 1:50 overnight; ZYMED™, Clinisciences™, Montrouge, France). Primary antibody was revealed with Alexa 594 donkey anti-mouse IgG conjugated to acridin red fluorochrome (dilution 1:100, Molecular Probes™, Invitrogen™, Cergy Pontoise, France). Nuclei were stained with Hoescht 33342 solution (0.125 mg/mL) (Sigma-Aldrich™) and visualized under a fluorescence microscope (Leica™, Bensheim, Germany). Negative controls consisted of staining with a non-specific mouse serum instead of the specific antibody. Counts of at least 500 cells/sample were systematically performed blindly in one experiment. The results were expressed as the mean±SEM of the number of stained cells.

Detection of Apoptosis

After 24 h of culture, HT-29 STD cells were treated during 24 h with the compounds A, B, C, D, F, at a concentration of 30 mM. 5-ASA (30 mM) and rosiglitazone (10-5 M) were used as positive controls. The molecules E and G were not included in this experiment due to their poor solubility. The pH of the drug solutions was adjusted to 7.4 with NaOH. Cells undergoing apoptosis were identified by enzymatic labelling of DNA strands using a terminal transferase dUTP nick end labelling assay (TUNEL assay, Roche Diagnostics™, Meylan, France). Counts of at least 500 cells/sample were systematically performed blindly in one experiment. The results were expressed as the mean±SEM of the number of stained cells.

Results

It has been observed that the molecules C and F induce PPARγ activation. Compound D also induces PPARγ, but to a slight lesser extent. Activation of PPARγ results in a cascade of reactions leading to a binding to specific DNA sequence elements termed peroxisome proliferator response elements (PPRE).

We investigated PPARγ transcriptional activity by transient transfections of epithelial cells with the renilla luciferase PPRE plasmids. Cells were stimulated with the different molecules during 24 hours. Analysis of PPARγ activity in transfected HT-29 cells showed that the compound C and F at a concentration of 30 mM increased the reporter gene activity by two-fold thereby displaying an activity similar to 5-ASA and rosiglitazone. Compounds A, B and G at a concentration of 30 mM exerted a rapid cytotoxic effect on epithelial cells limiting the investigation of PPARγ activation after 6 hours.

In particular, the molecules C, D and F induce PPARγ expression. In general all compounds A-G show the capacity to induce PPARγ expression at the protein levels in the HT-29 cell line. In particular, a mean 2-fold induction of PPARγ protein levels quantified by western blot was observed in cells treated during 24 hours with the molecules C, D and F.

In particular, the molecules C and F inhibit epithelial cell proliferation. We evaluated in HT-29 STD cell line the role of the molecules in the regulation of cell proliferation. Cell proliferation was assessed by nuclear protein Ki-67 staining expressed in proliferating cells, the presence of Ki-67 being necessary to maintain cell proliferation. Compared to untreated cells, incubation of HT-29 cells for 24 h with the molecules C and F (30 mM) resulted in a 67 to 75% inhibition of cell proliferation.

Similar results were obtained with the two positive controls rosiglitazone (10-5 M) and 5-ASA (30 mM) used at their optimal concentrations. Demonstration of the potential antimitogenic effect of the molecules A, B and D was limited by their rapid cytotoxic effects on epithelial cells at this concentration.

The compound F also induces epithelial cell apoptosis through PPARγ. Similarly to rosiglitazone and 5-ASA, the molecule F displayed apoptosis in 80% of epithelial cells identified by labelling DNA strand breaks using a terminal transferase dUTP nick end labelling (TUNEL). Similarly to the previous experiment, molecules A, B and D induced a rapid cytotoxic effect at 30 mM impeding cell apoptosis analysis.

Conclusion

This example specifically show the ability of compounds C and F to stimulate PPARγ expression and activation and to regulate epithelial cell proliferation and apoptosis. In addition, the cytotoxic effects on epithelial cells of compounds A, B D (as well as E to G) at 30 mM may be related to the presence in their structure of a highly reactive hydroxamic acid group known to display a great affinity for many various enzymes.

Example 6

Molecular Modelling

Molecular modelling studies were performed using SYBYL software version 6.9.1 (Tripos Associates Inc™, St Louis, Mo.) running on Silicon Graphics™ workstations. Three-dimensional model of the zwitterions form of 5-ASA was built from a standard fragments library, and its geometry was subsequently optimized using the Tripos force field. As the pKa of compounds is still unknown, the SPARC online calculator was used to determine the species occurring at physiological pH (7.4). Three-dimensional models of ionized compounds were built from a standard fragments library, and their geometry was subsequently optimized using the Tripos force field including the electrostatic term calculated from Gasteiger and Hückel atomic charges. The method of Powell available in Maximin2 procedure was used for energy minimization until the gradient value was smaller than 0.001 kcal/mol. Å. The structure of the human PPARγ ligand-binding domain was obtained from its complexed X-Ray crystal structure with the tesaglitazar (AZ 242) available in the RCSB Protein Data Bank (1I7I) (4,5). Flexible docking of the compounds into the receptor active site was performed using GOLD software. The most stable docking models were selected according to the best scored conformation predicted by the GoldScore and X-Score scoring functions. The complexes were energy-minimized using the Powell method available in Maximin2 procedure with the Tripos force field and a dielectric constant of 4.0 until the gradient value reached 0.01 kcal/mol. Å. The anneal function was used defining the ligand a hot region (10 Å).

Docking Studies

The compounds A to G fit tightly with the PPARγ-LBD interacting via hydrogen bonding with His-323, His-449, Tyr-473 and Ser-289 considered as key determinants required for molecular recognition and PPARγ activation.

It has shown that anti-inflammatory effects of compound falling in the formula (II) were mediated through PPARγ mainly expressed by epithelial cells. The docking analysis revealed that the mentioned compounds, used at a concentration of 30 mM, activate PPARγ, induce its expression by intestinal epithelial cells and exert a pharmacological action on the immune-inflammatory component of the celiac disease.

Conclusion

It has previously shown that anti-inflammatory effects of compounds of formula II with amino-salicylic structure (5-ASA structure like) were mediated through PPARγ, expressed in the epithelial cells at duodenum level. The rational development of the compounds A to G based on docking analysis revealed that said compounds, specifically C, F, used at a concentration of 30 mM, activate PPARγ and induce its expression by intestinal epithelial cells. The compounds also inhibit epithelial cell proliferation and induce apoptosis, two important mechanisms attributed to PPARγ activation. In particular, concerning the molecules A, B, D, G it has been detected that they have direct cytotoxic effects on epithelial cells at a concentration of 30 mM, impeding the analysis of PPARγ activation and regulation and evaluation of cell proliferation and apoptosis.

Example 7

Effects of Compounds H-Q of Formula (I) on PPARγ Activation

Materials and Methods

Materials

5-ASA was purchased at Sigma-Aldrich™ (St Quentin Fallavier, France). Rosiglitazone was acquired at Spi Bio™ (Massy, France). The following compounds H-Q, falling within the formula (I) were tested:

H

I

L

-continued

M

N

O

P

Q

Cell Lines

The colon carcinoma cell line HT-29 STD (ATCC HTB-38) was routinely grown in DMEM supplemented with 10% heat-FCS, and antibiotics. Cells were grown in monolayers, incubated at 37° C. in 5% CO2 and 95% relative humidity.

Transient Transfection with PPARγ and Stimulation of Cells

HT-29 STD cells were transiently transfected using the Effectene™ transfection reagent (Qiagen™) according to instructions from the manufacturer. To test PPARγ activation, we performed transfection with 500 ng of a minimal promoter construct containing two copies of PPRE obtained from the cytochrome p450 4A (2XCYP). The renilla luciferase plasmid (0.1 μg/well) was also transfected as an internal control for monitoring transfection efficiency and for normalizing the firefly luciferase activity. Transfected cells were left for 24 hours incubation at 37° C. Stimulations were performed after incubation of cells during 18 hours with the compounds H-Q at a concentration of 1 mM and compared with the two PPARγ synthetic ligands 5-ASA (30 mM) and rosiglitazone (10-5 M) used as positive controls. The pH of the drug solutions was adjusted to 7.4 with NaOH. Total cell extracts were prepared using the Passive Lysis Buffer (Promega™, Madison, Wis.). Luciferase activity was assayed in 20 μl of the extract using Promega's Dual Luciferase assay system according to manufacturer's protocol. Transfections were assayed in triplicate in at least three separate experiments. The luciferase activity was expressed as fold of the activity obtained in cells treated with the different molecules dividing by luciferase activity from non stimulated cells.

Results

Activation of PPARγ results in a cascade of reactions leading to a binding to specific DNA sequence elements termed peroxisome proliferator response elements (PPRE).

We investigated PPARγ transcriptional activity by transient transfections of epithelial cells with the renilla luciferase and PPRE plasmids. To evaluate if the compounds H-Q have efficacy as wells as or even over 5-ASA to stimulate PPARγ activation, we tested these molecules at a concentration of 1 mM. Effect of the new molecules at a concentration of 1 mM was compared to 5-ASA and rosiglitazone, used as positive controls at optimal concentrations of 30 mM and 10-5 M respectively. Cells were stimulated with the different molecules during 24 hours.

Analysis of PPARγ activity in transfected HT-29, cells showed that said compounds 40 at 1 mM increased the reporter gene activity by 4.8±0.71; 2.73±0.31; 2.64±0.46; 3.4±0.97 fold respectively, thereby displaying an activity similar or superior to 5-ASA at 30 mM (2.8±0.7) and rosiglitazone at 10-5 M (3.17±0.29).

There are evidences of the ability of the molecules H-Q falling in compounds the formula (I) of the invention, to increase the PPARγ activity in transfected HT-29 cells, displaying an activity similar or even superior to 5-ASA at 30 mM and rosiglitazone at 10-5 M.

The Italian Patent application no. MI2007A2429, including description, claims and drawings, filed on 24 Dec. 2007, whose priority is hereby claimed, is fully incorporated by reference.

The invention claimed is:

1. A method of treatment of the immune-inflammatory component of celiac disease comprising,
administering to a patient in need thereof, a therapeutically effective amount of a composition comprising a compound of formula (I) or pharmaceutically acceptable salts or esters thereof wherein $R_1$ and $R_2$, equal or different from each other, are selected from the group comprising —H or a linear or branched alkyl group having 1 to 6 carbons,

Y and Z, equal or different from each other, are selected from the group comprising —H, —OH, —COOH, $OR_3$, —CH($OR_3$)COOH, and wherein $R_3$ is selected from H, a linear or branched alkyl group having 1 to 6 carbons, wherein administration of the composition treats the disease, and wherein said compound is selected from the group consisting of:

-(±) 3-(3'-aminophenyl)-2-hydroxy-propionic acid of formula

2-(4-aminophenyl)-2-methoxyacetic acid,
2-(3-aminophenyl)-2-ethoxyacetic acid,
2-(4-aminophenyl)-2-ethoxyacetic acid,
3-(4'-aminophenyl)-2-methoxypropionic acid of formula 3-(4'-aminophenyl)-2-ethoxypropionic acid of formula 3-(3'-aminophenyl)-2-methoxypropionic acid of formula and

3-(3' aminophenyl)-2-ethoxypropionic acid of formula

2. A method of treatment of the immune-inflammatory component of celiac disease comprising, Administering to a patient in need thereof, a therapeutically effective amount of a composition comprising derivatives of 5-aminosalicylic acid selected from the group consisting of:

and their pharmaceutically acceptable salts or esters.

* * * * *